United States Patent
Probst et al.

(10) Patent No.: US 6,309,885 B1
(45) Date of Patent: Oct. 30, 2001

(54) PREPARATION OF BLOOD SAMPLES FOR DETECTING HOMOCYSTEINE AND/OR FOLATE

(75) Inventors: Reiner Probst, Munich; Matthias Blümke, Trier, both of (DE)

(73) Assignee: Reinee Probst, Munich (DE)

( * ) Notice: Subject to any disclaimer, the term of this patent is extended or adjusted under 35 U.S.C. 154(b) by 0 days.

(21) Appl. No.: 09/405,549

(22) Filed: Sep. 24, 1999

Related U.S. Application Data

(63) Continuation of application No. PCT/EP98/01830, filed on Mar. 27, 1998.

(30) Foreign Application Priority Data

Mar. 27, 1997 (DE) ................................. 197 13 088

(51) Int. Cl.$^7$ ..................... G01N 33/48; G01N 33/49
(52) U.S. Cl. ..................... 436/63; 436/86; 436/174; 436/176
(58) Field of Search ............... 436/63, 174, 176, 436/86

(56) References Cited

U.S. PATENT DOCUMENTS

| | | | |
|---|---|---|---|
| 3,972,991 | * 8/1976 | Caston et al. | 436/119 |
| 4,940,658 | * 7/1990 | Allen et al. | 435/4 |
| 5,434,087 | * 7/1995 | Beggs et al. | 436/505 |
| 5,478,729 | 12/1995 | Van Atta et al. | |
| 5,559,038 | 9/1996 | Kolhouse et al. | |
| 5,998,191 | * 12/1999 | Tan et al. | 435/22 |
| 6,020,206 | * 2/2000 | Vargeese et al. | 436/89 |
| 6,107,100 | * 8/2000 | Dabovic | 436/119 |

FOREIGN PATENT DOCUMENTS

| | | |
|---|---|---|
| 41 32 587 | 9/1991 | (DE). |
| 43 30 213 | 3/1995 | (DE). |
| 0486118 | 5/1992 | (EP). |
| WO 93/15220 | 8/1993 | (WO). |

OTHER PUBLICATIONS

"Measurement of Homocysteine Concentrations and Stable Isotope Tracer Enrichments in Human Plasama" MacCoss et al, May 1999.*

Ubbink et al., "Vitamin B–12, vitamin B–6, and folate nutritional status in men with Hyperhomocysteinemia[1–3]", Amer. Soc. For Clin. Nutr., 57:47–53, 1993.

Probst et al., "Stabilization of Homocysteine concentration in whole blood," Clin. Chem., 44:1567–1569, No. 7, 1998.

O'Broin et al., "Erythrocyte, Plasma, and Serum Folate: Speciment Stability before Microbiological Assay," Clin. Chem., pp. 522–524, 1980.

Israelsson et al., "Homocysteine in frozen plasma samples. A short cut to establish Hyperhomocysteinaemia as a risk factor for arteriosclerosis," Scand. J. Clin. Lab Invest, 53: 465–469, 1993.

Goyette et al., "Seven Novel Mutations in Methylenetetrahydrofolate Reductase Gene and Genotype/Phenotype Correlations in Severe Methylenetetrahydrofolate Reductase Deficiency," Am. J. Hum. Genet, 56: 1052–1059, 1995.

(List continued on next page.)

Primary Examiner—Jill Warden
Assistant Examiner—LaToya I. Cross
(74) Attorney, Agent, or Firm—Fitch, Even, Tabin & Flannery

(57) ABSTRACT

The invention relates to a method for preparing blood samples for detecting homocysteine and/or total folate and is characterized in that the blood sample is brought into contact with (a) at least one reagent for lysis of the blood cells, (b) at lease one inhibitor of the enzymes which produce and break down homocysteine, and optionally (c) at least one acid.

11 Claims, 3 Drawing Sheets

OTHER PUBLICATIONS

Malinow et al., "Population variation and genetics of plasma Homocyst(e)ine level," Clin. Genet., 41:315–321, 1992.

Clarke et al., Hyperhomocysteinemia: An Independent Risk Factor for Vascular Disease, The New Eng. J. of Med., 324: 1149–1155, Apr. 25, 1991.

Fiskerstrand et al., "Homocysteine and Other Thiols in Plasma and Urine: Automated Determination and Sample Stability," Clin. Chem., 39/2: 263–271, 1993.

Brattstrom et al., "Impaired homocysteine metabolism in early–onset cerebral and peripheral occlusive arterial disease," Atherosclerosis, 81: 51–60, 1990.

* cited by examiner

PREPARATION OF BLOOD SAMPLES FOR DETECTING HOMOCYSTEINE AND/OR FOLATE

This is a continuation, of prior application number PCT/EP98/01830, filed Mar. 27, 1998 designating The United States, which is hereby incorporated herein by reference in its entirety.

TECHNICAL FIELD

The present invention relates to a method and a blood-withdrawal vessel for preparing blood samples for detecting homocysteine and/or total folate. In particular, "preparation" is defined here as the stabilization of blood samples for the detection of homocysteine and the lysis of the erythrocytes in order to prepare the detection of total folate. In conjunction with this invention, "total folate" is defined as the sum of erythrocytic and plasma folate.

PRIOR ART

Homocysteine, a sulfur-containing amino acid, occurs in the organism only as an intermediate product in the methionine/cysteine/glutathione metabolic circulation and is not incorporated into proteins. Various hereditary defects of the key enzymes cystathionine-β-synthetase and methylene-tetrahydrofolate-reductase (MTHFR) or a deficiency of corresponding vitamin cofactors ($B_{12}$, $B_6$, folate) cause homocysteine to be insufficiently broken down and therefore it arises in increased concentrations in the plasma (K. Berg et al., Clin. Genet. (1992) 41:315–321; P. Goyette et al., Am. J. Hum. Genet. (1995) 56:1052–1059). Numerous clinical studies over the last few years were able to identify this hyperhomocysteinemia as a risk factor independent of lipid metabolism as regards atherosclerotic disorders and thrombo-embolic consequences thereof. 30–40% of patients who prematurely suffer a coronary (R. Clarke et al., N. Engl. J. Med. (1991) 324: 1149–1154) or a stroke (B. Israelsson et al., Scand. J. Clin. Lab. Invest. (1993) 53: 465:469), angina pectoris or peripheral arterio-occlusive disease (L. Brattström et al., Atherosclerosis (1990) 81: 51–60) exhibit an increased level of homocysteine. The prevalence of the homozygotic MTHFR defect accompanying an increased homocysteine level is given at 59, (Goyette et al., loc. cit.), which lies in the order of magnitude of the prevalence of diabetes mellitus in the entire Caucasian population.

Homocysteine is currently measured with the aid of HPLC (high-pressure liquid chromatography) from EDTA plasma and such a measurement can be performed with reasonable accuracy. It is nevertheless necessary to optimize the pre-analytics of the detection of homocysteine, because the in vitro release of this amino acid from the blood cells, which also continue to produce homocysteine in the withdrawal vessel after withdrawal of the blood and which release this substance from the cells as a result of an active transport process, may considerably distort detection in the plasma. For this purpose, it has so far been necessary to employ centrifugation so as to separate the cells from the plasma immediately after withdrawal of the blood. The homocysteine concentration in the plasma is then stable for at least 48 hours (T. Fiskerstrand et al., Clin. Chem. (1993) 39/2: 263–271). This complicated procedure cannot, however, be routinely performed in standard ward mode or by the General Practitioner (GP).

As a partial aspect, the present invention is therefore based on the problem of avoiding a significant homocysteine increase in the whole blood, an increase which naturally occurs within one to two hours of venous blood withdrawal (FIG. 1). The hitherto necessary and time-critical separation of the blood cells from the plasma can be avoided by the present invention, and the stabilization of the homocysteine concentration in the resultant lyzed blood can be reached over 48 hours.

It is already known that blood samples should be protected from coagulation by addition of specific reagents (NaF, EDTA, citrate) and stabilized against enzymatic breakdown processes. The use of these reagents in standard blood-withdrawal vessels, however, does not achieve any stabilization of the homocysteine concentration, since these enzyme inhibitors are not absorbed into the blood cells and consequently an intracellular inhibition of the enzyme that produces the homocysteine cannot be achieved (FIG. 1). Within two hours, the currently valid limit of 15 $\mu$mol/l (K. Rasmussen et al., Clin. Chem. (1996) 42:4 630–636), above which the risk of atherosclerosis increases significantly, is therefore already exceeded or virtually reached by samples exhibiting a very low initial concentration. This is evident from FIG. 1 which shows the significant increase of different initial homocysteine concentrations in the blood treated with NaF or EDTA at room temperature and at 4° C. This rise can amount to as much as 100% within 6 hours.

As stated above, the homocysteine concentration frequently correlates inversely with the folate concentration, since folate is a cofactor for the enzyme MTHFR that breaks down homocysteine. In consequence, folate is frequently given in order to return a pathologically elevated homocysteine concentration to the normal range. A detection of the basal and actual folate level in addition to the homocysteine level is therefore diagnostically appropriate. Since folate is mainly present and takes effect in the erythrocytes (approx. 98%), the detection of the erthyrocytic folate or total folate is more conclusive than the usual detection of the plasma folate or serum folate. The present invention is therefore based on the further problem of preparing a blood sample such that the concentration of total folate can be immediately detected in addition to or instead of the homocysteine concentration.

DESCRIPTION OF THE INVENTION

In accordance with the invention, the above objects are solved by a method for preparing blood samples for detecting homocysteine and/or total folate, in which method the blood sample is brought into contact, during or immediately after withdrawal of blood, with a) at least one reagent for lysis of the blood cells and b) at least one inhibitor of the enzymes which produce and break down homocysteine.

Particular preference is also placed on bringing the blood sample into contact with c) one or more acids.

The invention is also directed at a blood-withdrawal vessel for preparing blood samples, particularly for detecting homocysteine and/or total folate, this blood-withdrawal vessel comprising a) at least one reagent for lysis of the blood cells and b) at least one inhibitor of the enzymes which produce and break down homocysteine and preferably c) one or more acids.

The dependent claims relate to other preferred embodiments.

THE BEST APPROACH TO IMPLEMENTING THE INVENTION

The reagent for lysis of the blood cells a) may particularly be a detergent, as well as for example ascorbic acid. An anionic detergent such as sodium dodecyl sulfate (SDS) is suitable, but a nonionic detergent such as Nonidet P40 (octyl phenol ethylene oxide condensate having on average 9 mol ethylene oxide per mol phenol) or Triton X is preferably used. Liquid detergents have proved particularly practical. Particular preference is placed on the detergent's use in undiluted form, as supplied by the manufacturer. Mixtures of two or more detergents can also be used.

Possible inhibitors of those enzymes b) which produce and break down homocysteine particularly include those which form chelate complexes with calcium. Such inhibitors include, inter alia, citrates and other chelating agents, e.g. di- or polycarboxylic acids, aminocarboxylic acids or phosphonocarboxylic acids and salts thereof, particularly the alkali salts. Preference is given to ethylene diamine tetraacetic acid disodium salt (EDTA) which is used with particular preference in the form of a highly concentrated aqueous solution just below the saturation limit.

If lysis of the blood cells occurs with the aid of a highly concentrated detergent while EDTA simultaneously inhibits the released enzymes immediately after withdrawal of blood, this prevents the homocysteine concentration from increasing. An approx. 10% drop in homocysteine concentration in the course of 24 hours was nevertheless observed in this case—such a decrease also slightly distorts the result.

Figure 2:
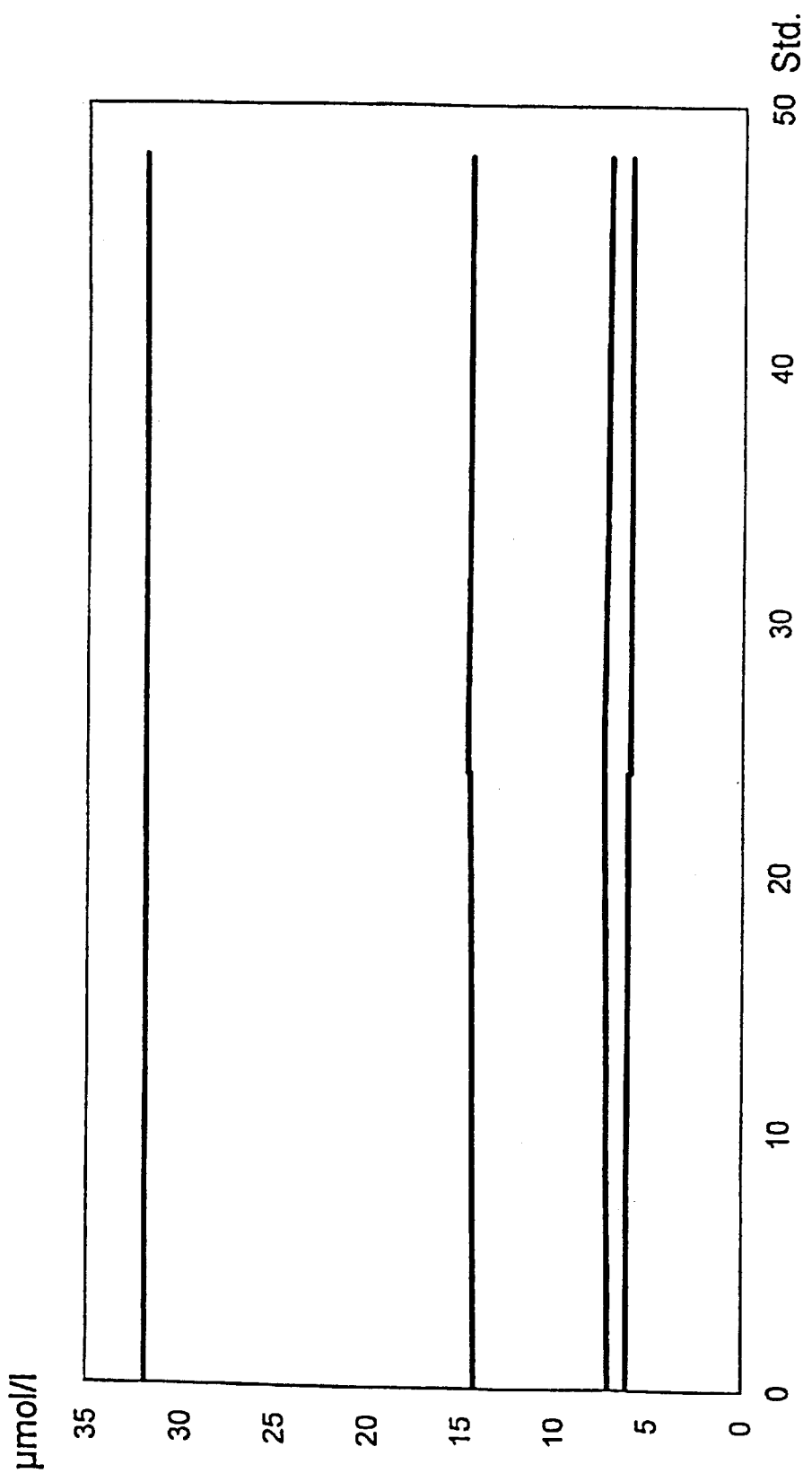
FIG. 2 shows the time course of the homocysteine concentration in blood-withdrawal vessels according to the present invention.

It was surprisingly found that this slight distortion can also be prevented by addition of an acid, particularly an acid which causes the pH to drop by at least 2 units. Ascorbic acid, acetic acid, hydrochloric acid and preferably citric acid are possible, inter alia, as such acids. Particular preference is given to the use of citric acid as a highly concentrated aqueous solution. In combination with Nonidet P40 and EDTA, the citric acid results in an almost perfect stabilization of the homocysteine concentration in the lysate over 48 hours (FIG. 2). As part of analytical intra-assay imprecision, it was possible to determine neither an increase nor a decrease in the homocysteine concentrations. FIG. 2 shows the time course of varyingly high homocysteine concentrations in the stabilized lysate over 48 hours. It was shown that these concentrations remained constant within ±2%.

The total folate concentration can also be detected from the same sample in the blood-withdrawal vessel according to the invention by means of an immuno-assay system (e.g. manufactured by Sanofi Diagnostics Pasteur). It is evident from Example 2 that the total folate concentrations measured in the lysate directly stabilized during the withdrawal are comparable to those folate concentrations measured conventionally in the laboratory after introduction of an aliquot of EDTA whole blood into charged lysis reagent. The timing of the lysis of the whole blood therefore does not have any effect on the total folate concentration. According to the prior art, however, the withdrawal of two blood samples was usually necessary in order to detect both the homocysteine and the total folate concentration, because the homocysteine sample had to be immediately centrifuged. In this respect, the present invention simplifies the approach as far as the doctor and patients are concerned.

The applicability of the method according to the invention and of the blood-withdrawal vessel for preparing blood for standard HPLC analysis methods, without having to modify them, makes it easier for the laboratory analyst to interpret the values reliably, since an incorrect pre-analytical treatment of the samples (the whole blood is left to stand for too long) can be ruled out. It is also possible to dispense with the sample material's immediate centrifugation, which is usually impossible in clinical wards or the practices of doctors.

This consequently rules out the detection of incorrectly high homocysteine values in the laboratory, which values may entail follow-up costs as a result of more extensive analyses or which may disconcert patients. Bearing in mind the high prevalence (5% in the case of MTHFR defect) of pathologically elevated plasma homocysteine concentrations in the Caucasian population as a whole and the possibility of simply treating this risk factor with folic acid, it will be necessary to expect a high volume of samples (J. B. Ubbink et al., Am. J. Clin. Nutr. (1993) 57:47–53). The avoidance of the need for complicated and interference-prone pre-analytics (time-critical centrifugation) might save such high follow-up costs in the health sector.

Particular preference is placed on charging the reagents in commercially available blood-withdrawal vessels, e.g. a Monovette® (manufactured by Sarstedt) or a Vacutainer® (manufactured by Becton Dickinson). Monovettes® with EDTA, NaF, heparin etc. fillings are for example already commercially available. It is immediately possible to fill a corresponding container with the reagents according to the invention, thus making available a blood-withdrawal vessel according to the invention. The sample container may, for example, comprise polyethylene or another suitable plastic and be present in the form of a syringe. A stamp is used to transport the blood from the vein into the blood-withdrawal vessel via a hypodermic needle as a result of generating a partial vacuum. A pre-evacuated vessel with a hypodermic needle can alternatively be used. A "Blood-withdrawal vessel" as defined by the invention is also understood as a capillary blood withdrawal system, e.g. a glass capillary, combined with a vessel in which the capillary blood is stored until preparation for the purpose of measurement. Such systems are already on the market. In this instance, the reagent combination according to the invention is usually present in the storage vessel of this capillary blood withdrawal system.

The preferred combination of Nonidet P40, EDTA and citric acid is also advantageous in that it comprises inexpensive components that are already individually used in the field of clinical chemistry. When combined, the reagents are stable at room temperature and retain their effect.

Figure 3:
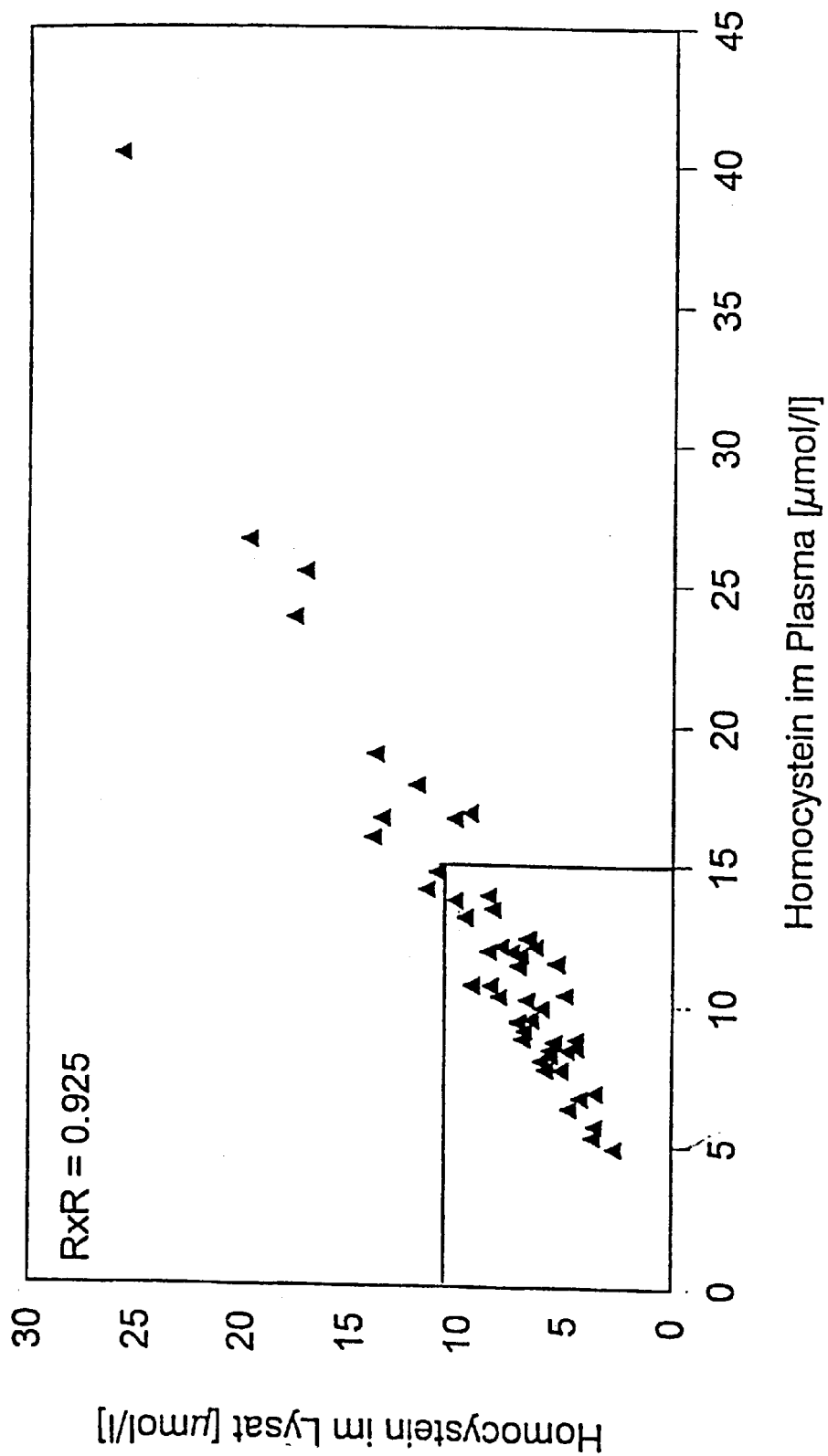
FIG. 3 shows the correlation of the plasma and lysate homocysteine concentrations.

To check the correlation of the homocysteine concentrations of lysate and plasma samples, these were measured in parallel. As expected, the homocysteine concentrations in the lysate are lower because the homocysteine concentration in the blood cells, compared to the same volume of plasma, is lower. A very good correlation can nevertheless be found between plasma and lysate homocysteine concentrations (FIG. 3, $R^2=0.92$). This makes it possible to assign a lysate cut-off of 11 $\mu$mol/l which is comparable to the cut-off in the plasma of 15 $\mu$mol/l described in the literature (K. Rasmussen et al., Clin. Chem. (1996) 42:4 630–636).

The method described above can be used to achieve stabilization of the homocysteine concentration in lysed blood by means of standard, inexpensive and stable reagents and consequently to increase the reliability of the atherosclerosis risk prediction. Due to the increasing significance of this parameter based on evaluations of studies over the last few years, a high volume of samples will be expected in future. The specially prepared blood-withdrawal vessels assist the doctor and medical personnel to save time and help the laboratory analyst to detect reliable homocysteine values.

The present invention will now be explained on the basis of two exemplary embodiments.

EXAMPLE 1

An EDTA Monovette® (volume 2.7 ml, EDTA=approx. 1 mg/ml blood), Sarstedt company, is filled with 25 μl Nonidet P40 (undiluted), 50 μl EDTA (c=70 g/l, 1.3 mg/ml blood) and 25 μl citric acid (c=0.6 g/ml, 5.6 mg/ml blood). 2.7 ml whole blood is added to this Monovette and shaken. The container is then left to stand at room temperature and the homocysteine concentration is detected at intervals (0 h, 24 h, 48 h) by HPLC. It is evident from FIG. 2 that the homocysteine concentration virtually does not vary over time. This stipulation represents currently the best implementation of the invention.

Figure 1:
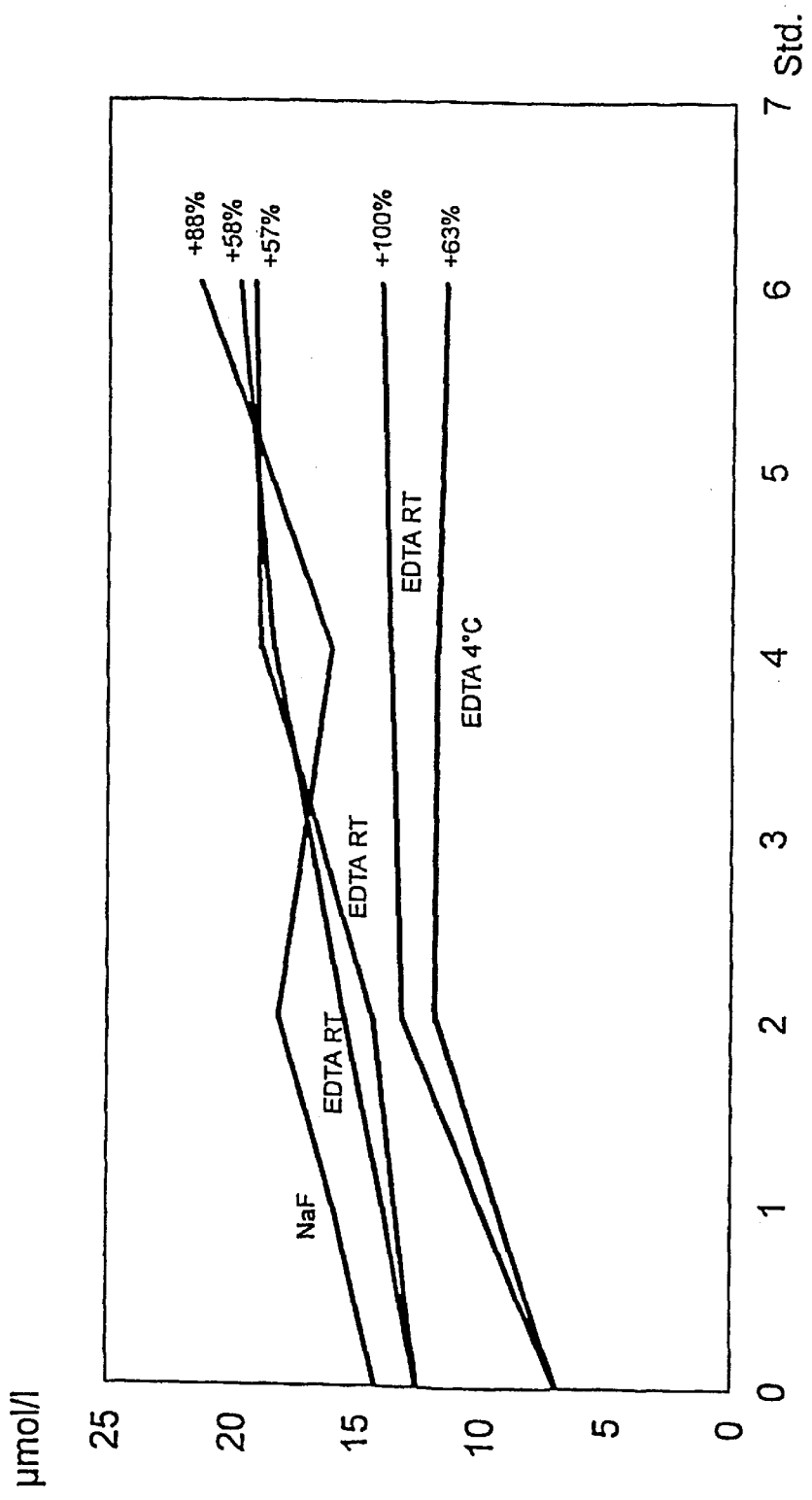
FIG. 1 shows the time course of the homocysteine concentration in blood-withdrawal vessels according to the prior art.

By way of comparison, EDTA and NaF Monovettes® (volume 2.7 ml) were filled with 2.7 ml whole blood and left to stand for several hours at room temperature. FIG. 1 shows that the homocysteine concentration in the whole blood significantly increases without the stabilization technique according to the invention.

EXAMPLE 2

Based on an EDTA Monovette® prepared in accordance with the invention and listed in Example 1, the total folate concentration is detected using an "Access Immuno-Assay System" manufactured by Sanofi Diagnostics Pasteur. The resultant values are compared with the total folate concentrations of blood samples prepared by subsequent lysis of EDTA blood in the laboratory using a charged lysis reagent from the aforementioned company. Table 1 below shows the good correlation of the folate concentrations.

TABLE 1

| Folate concentration in the lysate [ng/ml] Blood-withdrawal system according to the invention | Folate concentration in the subsequently lysed EDTA blood [ng/ml] Routine detection as prescribed in the access assay |
| --- | --- |
| 54 | 55 |
| 79 | 83 |
| 131 | 137 |
| 260 | 283 |

What is claimed is:

1. A method of preparing blood samples for detecting homocysteine and/or total folate, wherein a blood sample is brought into contacts during or immediately after blood withdrawal, with:

a) at least one reagent for lysis of blood cells, b) at least one inhibitor of enzymes which produce and break down homocysteine, wherein the reagent for lysis of blood cells and the at least one inhibitor of enzymes which produce and break down homocysteine are effective for stabilizing homocysteine levels in the blood sample.

2. A method according to claim 1, wherein the blood sample is further brought into contact, during or immediately after blood withdrawal, with: c) one or more acids.

3. A method according to claim 1, wherein the reagent for lysis of the blood cells is an octyl phenol ethylene oxide condensate having an average 9 mole ethylene oxide per mole phenol.

4. A method according to claim 1, wherein EDTA is used as an inhibitor of the enzymes which produce and break down homocysteine.

5. A method according to claim 2, wherein citric acid is used as an acid.

6. A method of preparing blood samples for detecting homocysteine and/or total folate, wherein a blood sample is brought into contact, during or immediately after blood withdrawal, with:

a) octyl phenol ethylene oxide condensate; and b) at least one inhibitor of enzymes which produce and break down homocysteine, wherein the octyl phenol ethylene oxide condensate and the at least one inhibitor of enzymes which produce and break down homocysteine are effective for stabilizing homocysteine levels in the blood sample.

7. The method of claim 6 wherein the inhibitor of enzymes is EDTA.

8. The method of claim 6 wherein blood sample is further brought into contact, during or immediately after blood withdrawal with citric acid.

9. A method of preparing blood samples for detecting homocysteine and/or total folate, wherein a blood sample is brought into contact, during or immediately after blood withdrawal, with:

a) at least one reagent for lysis of blood cells;

b) at least one inhibitor of enzymes which produce and break down homocysteine; and c) at least one additional acid;

wherein the reagent for lysis of blood cells and the at least one inhibitor of enzymes which produce and break down homocysteine are effective for stabilizing homocysteine levels in the blood sample.

10. The method of claim 9 wherein the inhibitor of enzymes includes EDTA.

11. The method of claim 9 wherein the additional acid is citric acid.

* * * * *